(12) United States Patent
Williams et al.

(10) Patent No.: US 9,737,671 B2
(45) Date of Patent: Aug. 22, 2017

(54) TROCAR ASSEMBLIES

(71) Applicants: Steven Williams, St. Paul, MN (US); Brandon Lee Michal, White Bear Lake, MN (US); Nathanial Tran, Lakeville, MN (US)

(72) Inventors: Steven Williams, St. Paul, MN (US); Brandon Lee Michal, White Bear Lake, MN (US); Nathanial Tran, Lakeville, MN (US)

( * ) Notice: Subject to any disclaimer, the term of this patent is extended or adjusted under 35 U.S.C. 154(b) by 0 days.

(21) Appl. No.: 13/986,120

(22) Filed: Apr. 3, 2013

(65) Prior Publication Data
US 2014/0303550 A1 Oct. 9, 2014

Related U.S. Application Data

(60) Provisional application No. 61/687,231, filed on Apr. 20, 2012.

(51) Int. Cl.
*A61M 5/158* (2006.01)
*A61M 5/32* (2006.01)
*A61B 17/34* (2006.01)

(52) U.S. Cl.
CPC ....... *A61M 5/3297* (2013.01); *A61B 17/3421* (2013.01); *A61B 17/3474* (2013.01); *A61M 5/329* (2013.01)

(58) Field of Classification Search
CPC .......... A61M 5/158; A61M 2005/1585; A61M 2005/006; A61M 2039/0626; A61M 13/00; A61M 25/0021; A61M 25/0023; A61M 25/0041; A61M 29/00; A61B 17/3424
See application file for complete search history.

(56) References Cited

U.S. PATENT DOCUMENTS

| | | | | |
|---|---|---|---|---|
| 5,271,414 | A * | 12/1993 | Partika et al. | 600/567 |
| 5,545,150 | A | 8/1996 | Danks | |
| 6,840,900 | B2 * | 1/2005 | Smith | 600/104 |
| 6,849,062 | B2 * | 2/2005 | Kantor | A61M 25/0023 604/103.04 |
| 7,833,203 | B2 * | 11/2010 | Sherman | A61B 1/00075 600/139 |
| 2005/0267448 | A1 * | 12/2005 | Bonnet | A61B 17/3417 606/1 |
| 2005/0283125 | A1 * | 12/2005 | Barkhahn | A61L 31/14 604/272 |
| 2007/0149950 | A1 * | 6/2007 | Perkins | A61F 9/00745 604/524 |
| 2008/0009797 | A1 | 1/2008 | Stelon | |

(Continued)

FOREIGN PATENT DOCUMENTS

WO  WO 2008-106085  9/2008
WO  WO 2010-044051  4/2010

*Primary Examiner* — Quynh-Nhu H Vu
(74) *Attorney, Agent, or Firm* — Jacobson and Johnson LLC; Thomas N. Phung

(57) ABSTRACT

A trocar assembly wherein a trocar with an elongated polygonal tube can receive either an obturator or a medical instrument of a dissimilar cross-sectional shape with the medical instrument of the different cross sectional shape maintable in a central condition therein to inhibit pressure losses to lateral flow to thereby permit use of a cannula having a smaller cross sectional area than a cylindrical cannula as well as inhibit trauma to an entry site around the cannula.

7 Claims, 3 Drawing Sheets

(56) References Cited

U.S. PATENT DOCUMENTS

2010/0318033 A1    12/2010  Lam
2010/0324488 A1*  12/2010  Smith ...................... 604/164.11
2011/0201887 A1*   8/2011  Greenblatt et al. ........... 600/130

* cited by examiner

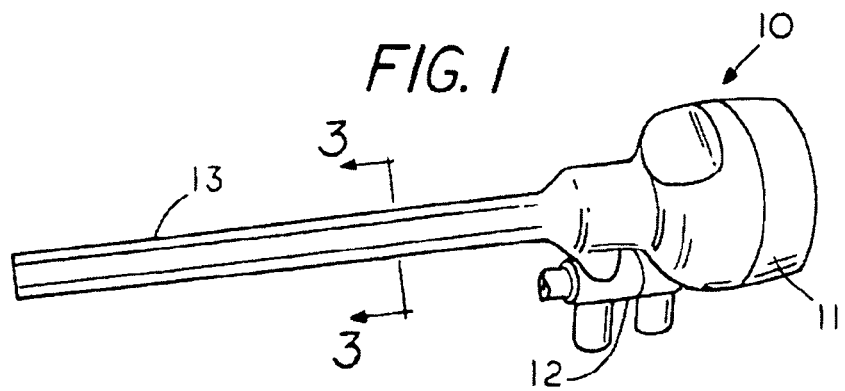
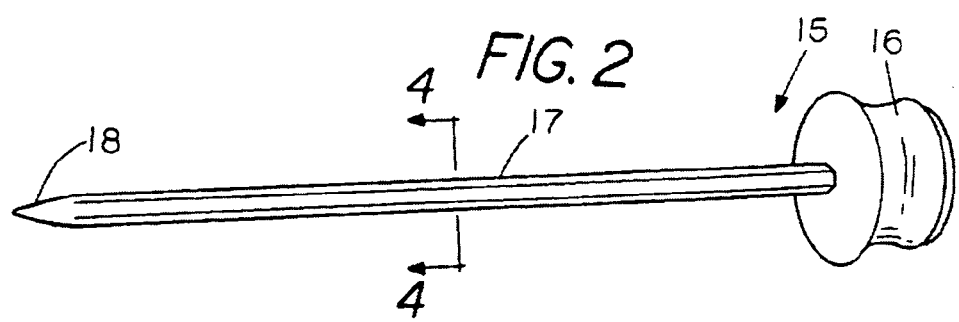
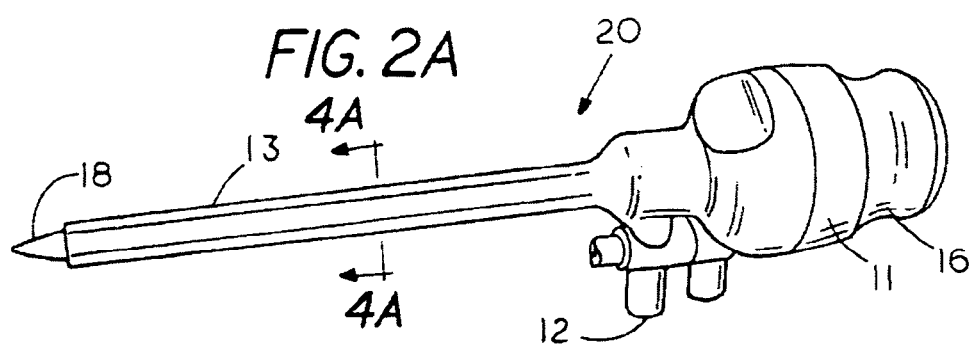

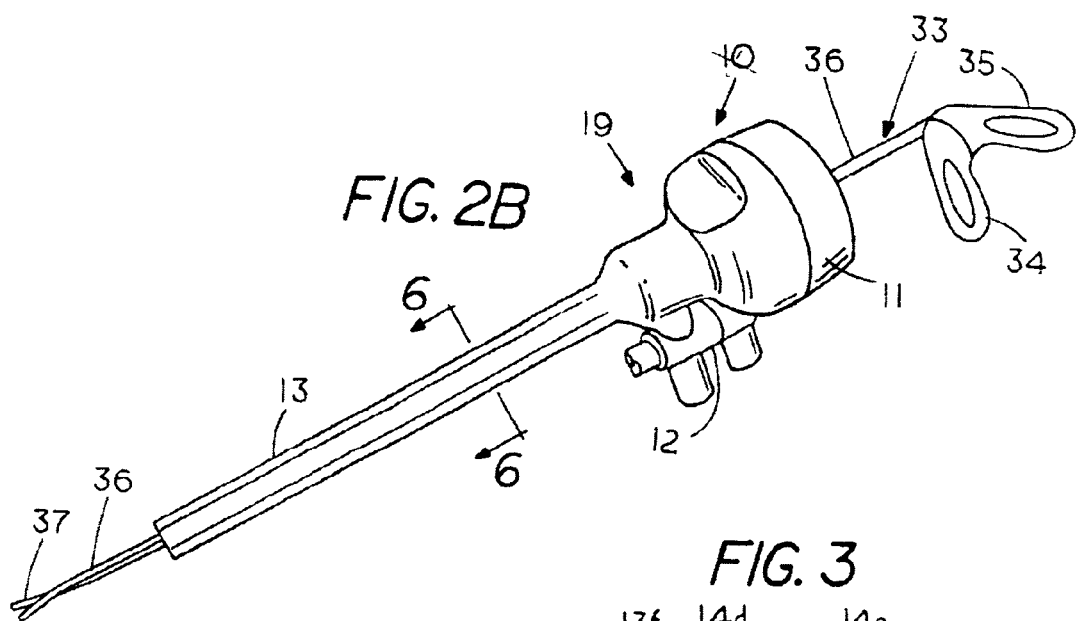
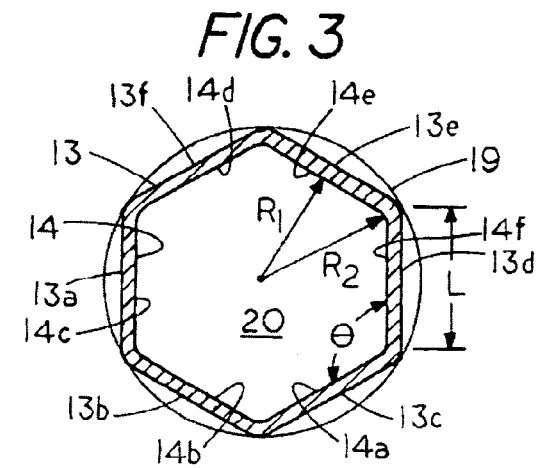
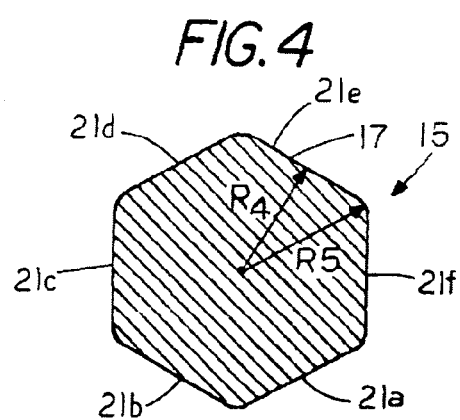
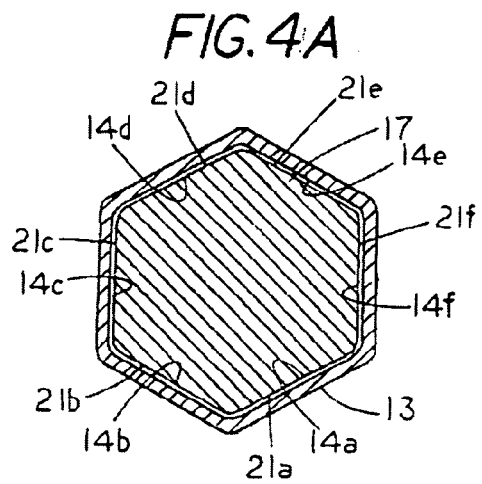

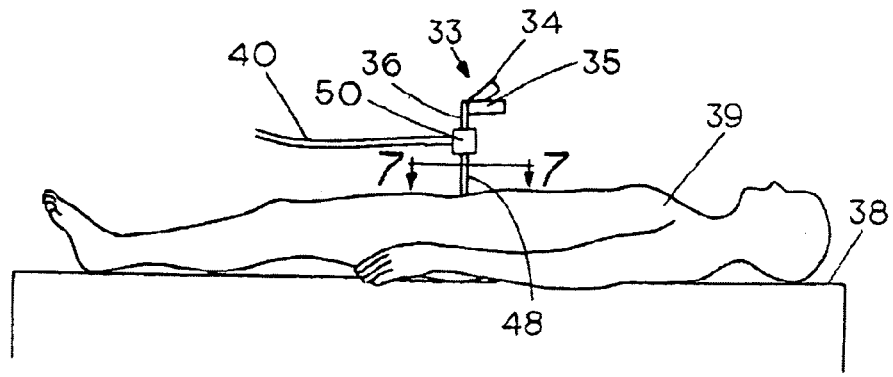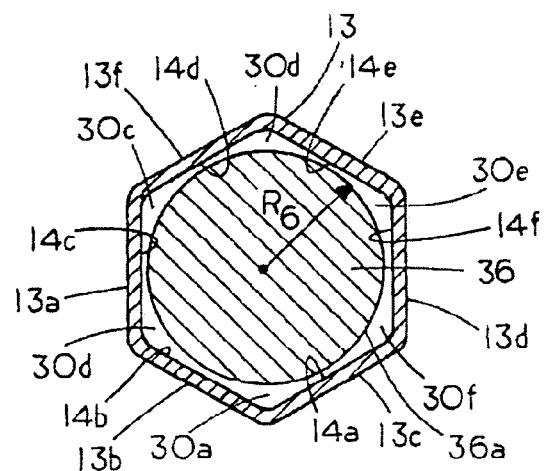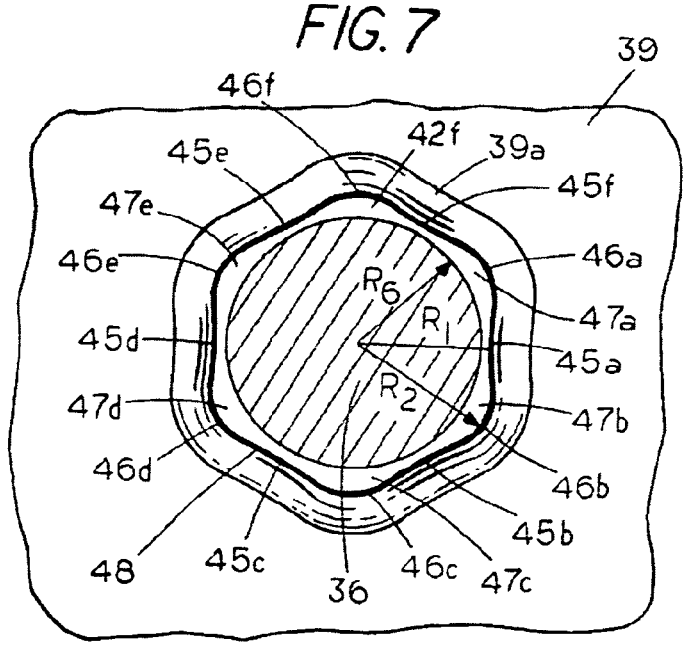

TROCAR ASSEMBLIES

CROSS REFERENCE TO RELATED APPLICATIONS

This application claims priority from provisional application Ser. No. 61/687,231 filed Apr. 20, 2012

STATEMENT REGARDING FEDERALLY SPONSORED RESEARCH OR DEVELOPMENT

None

REFERENCE TO A MICROFICHE APPENDIX

None

BACKGROUND OF THE INVENTION

Medical gasses are used to distend, or insufflate, a body cavity in order to produce a suitable void in the body cavity, which enables a surgeon to perform a minimally invasive surgical procedure on a patient. For example, in laparoscopic surgery or other types of invasive medical procedures one of the surgical goals is to minimize trauma to the tissue surrounding the entry port into the body cavity though the use of a cannula. Typically, during laparoscopic surgery, a surgeon manipulates an instrument inside of the patient through the cannula, which extends through the body tissue and into the body cavity of a patient. Carbon dioxide, which is the most prevalent insufflation gas used in laparoscopic surgery, is also present in the cannula since it flows into the patient's body cavity through the cannula while an insufflator regulates the rate of delivery of the carbon dioxide insufflation gas. Typically, the insufflator, which receives its medical insufflation gas from a medical grade canister, transports the medical insufflation gas to the cannula via a fluid conduit. An oversized cylindrical cannula provides an annular gas flow passage between the interior surface of the cannula, which usually has a cylindrical shape, and the exterior surface of the medical instrument, which also usually has a cylindrical shape.

In order to reduce the trauma to a patient one may want to reduce the diameter of the oversized cannula, which surrounds the medical instrument. Unfortunately, the reduction of the diameter of the oversized cannula, which is beneficial since it reduces trauma around the tissue pierced by the cannula, causes other problems since the medical devices and surgical instruments introduced into a lumen in the cannula increase the obstruction to the flow of the insufflation gas that enters the body cavity through the same lumen in the cannula. If a small surgical instrument is placed within a cannula of reduced diameter the flow obstruction may not be significant, however, with the use of larger and more complex surgical instruments in a cannula, which is no longer oversized, the pressure losses or pressure drop created by the annular like passage located between the interior surface of the cannula and the exterior surface of the medical instrument may have adverse consequences if one wants to maintain the body cavity in an inflated condition as well as the medical instrument in a sealed relationship to the cannula.

SUMMARY OF THE INVENTION

A trocar assembly having an elongated polygonal cannula for holding either an obturator or a medical instrument therein in a slidingly interdisposed condition. The medical instrument is slidably and rotationally interfitted within the cannula while the obturator is slidably but rotationally engageable with the cannula. The elongated cannula has an external shape allowing plastic flow of body tissue there around to minimize trauma to a wound site surrounding the cannula. With a medical instrument located in the elongated polygonal cannula the exterior radial surface of the medical instrument and the interior surface of the cannula, which are of dissimilar cross sectional shape, coact to define a set of peripheral fluid passages therebetween for introducing an insufflation gas into a distended body cavity so that one can maintain the body cavity in a distended condition during the a medical procedure within the body cavity. The use of dissimilar shapes of the cannula and the medical instrument enables the internal surfaces of the cannula to form a centering guide to maintain the medical instrument in a central position to lessen the chances of disturbing the seal between the trocar and the medical instrument as well as minimizing pressure losses. The use of dissimilar shapes of the cannula also allows one to reduce the trauma to the body tissue surrounding a cannula entry port into a body cavity by allowing use of a smaller cannula. The cannula may be made from a transparent material with a surface coating or surface finish on the interior that normally renders the cannula opaque but in response to moisture in the insufflation gas increases the transparency of the cannula to provide a visual monitoring of the presence of insufflation gas flow through the cannula.

BRIEF DESCRIPTION OF THE DRAWINGS

FIG. 1 is a perspective view of a trocar with the cannula comprising an elongated polygonal instrument tube;

FIG. 2 is a perspective view of an obturator;

FIG. 2A is a perspective view of a trocar assembly with the obturator located within the cannula;

FIG. 2B is a perspective view of a trocar assembly with a medical instrument located within the cannula;

FIG. 3 is a cross sectional view of the polygonal cannula of FIG. 1;

FIG. 4 is a cross sectional view of the obturator shown in FIG. 2;

FIG. 4A is a cross sectional view taken along lines 4A-4A of FIG. 2 of an obturator having a polygonal shape located in a polygonal cannula;

FIG. 5 shows a cannula with a medical instrument extending into the body of a patient;

FIG. 6 is a cross sectional view showing the interrelation of a set of elongated peripheral fluid passages located between the medical instrument and the interior of the polygonal cannula; and FIG. 7 is a sectional view of the trocar assembly taken along lines 7-7 of FIG. 5 showing deformed body tissue surrounding the exterior of the elongated polygonal cannula.

DESCRIPTION OF THE PREFERRED EMBODIMENT

FIG. 1 is a perspective view of a trocar 10 with a cannula comprising an elongated polygonal instrument tube 13 connected to housing 11, which includes a stopcock 12 for controlling ingress of insufflation gas into the trocar 10. The cannula may be made from a variety of rigid materials including opaque materials or transparent materials, which contains a surface coating or surface finish on the interior surface of the cannula that normally renders the cannula opaque but in response to moisture in the insufflation gas increases the transparency of the cannula through wetting of the surface coating.

FIG. 2 is a perspective view of an obturator 15 comprising an elongated shaft 17 having a conical tip 18 for piercing through body tissue to enable insertion of the distal end of the cannula 13 into a body cavity to enable a surgeon to perform a medical procedure through external manipulation of a medical instrument extending through a working channel or lumen in the cannula 13.

FIG. 2A shows a trocar assembly 20 comprising the trocar 10 of FIG. 1 and the obturator 15 of FIG. 2 in an assembled condition. The drawing shows the conical body piercing tip 18 projecting axially outward beyond the distal end of the cannula 13 and the head 16, which may have a higher coefficient of friction to provide an enhanced grip. The tip 18, which extends out the opposite end of the trocar may have a low friction surface coating thereon to optimize the ability to permit a surgeon to force the tip 18 through the body tissue. Once the cannula 13 is inserted into the patient the obturator 15 is removed and is replaced by a medical instrument that can be manipulated by a surgeon from a position external to a body cavity.

FIG. 2B shows a trocar assembly 19 comprising the trocar 10 of FIG. 1 together with an example of a typical surgical instrument 33. Surgical instrument 33 includes an elongated cylindrical shaft 36 for extending through cannula and handles 34 and 35 for use in manipulation of the jaw 36 and jaw 37, which are located on the distal end of the surgical instrument 33.

FIG. 5 shows an example of use of trocar assembly 19, which comprises a cannula 13 and a medical instrument 33 having handles 35, 34 located outside the body cavity of a patient 39 supported by an operating table 38. As used herein the term trocar assembly may refer to the trocar cannula 13 with either an obturator 15 located therein or a medical instrument 33 located therein where the medical instrument is used for performing a surgical procedure within a body cavity with controls for the medical instrument located external to the body cavity. In this example a tube 40, which is connected to a source of insufflation gas, supplies the insufflation gas to the patient 39 through the trocar cannula 13 which also contains the medical instrument therein.

FIG. 3 is a cross sectional view of the cannula 13, which comprises an elongated polygonal tube 13, that extends outward from the housing 11. In the example shown in FIG. 3 the elongated polygonal tube 13 has the cross sectional shape of a regular cyclic hexagon which is both an equiangular and equilateral polygon having equal corner angles Θ, sides or webs 13a-f of the same length $L_1$, as well as having all the corners located on a single reference circle 9. A working channel 20 or lumen extends longitudinal through the polygonal tube 13. For reference the distances from a geometric center of the tube 13 to a web, which forms a side of the polygon, is designated by $R_1$ and the distance from the geometric center of the tube 13 to the junction of adjacent webs is designated by $R_2$ with the dimension $R_2$ being greater than $R_1$.

FIG. 4 shows a cross sectional view of obturator 15 revealing that the obturator 15 has an exterior hexagonal shape 17 with external sides 21a-f. For reference purposes the distance from the geometric center of the obturator 15 to a flat located between adjacent corners is designated by $R_4$ and the distance from the geometric center to a corner located between adjacent flats is designated by $R_5$ with $R_5$ being greater than $R_4$.

To illustrate the interrelation of the obturator 15 and the cannula 13 reference should be made to FIG. 4A which shows a cross section view taken along lines 4A-4A of FIG. 2A revealing the obturator 15 having its outer surfaces 21a-f located in a spaced condition from the inner web faces 14a-f of the polygonal tube 13. In this example the obturator dimensions $R_4$ and $R_5$ are respectively less than the cannula dimensions $R_1$ and $R_2$ such that the obturator is slidably disposed within cannula 13. On the other hand the differences in the dimensions are sufficiently small so that the obturator outer web surfaces 21a-f are rotationally engageable with the cannula interior web faces of 14a-f to enable a surgeon to simultaneously rotate the trocar assembly 20 i.e. the cannula 13 and the obturator 15, as a unit as the cannula 13 and obturator 15 are forced through a patients body tissue and into the body cavity of the patient.

FIG. 6 is a cross sectional view of the trocar assembly 19 of FIG. 2B taken along lines 6-6 to illustrate in isolated form a feature of the invention that minimizes the trauma to a patient during a medical procedure as well as maintaining a medical instrument 36 in proper alignment within the cannula 13. In the example shown the circular medical instrument 32 has a diameter $2R_6$ which is sufficiently less than a web to web dimension $2R_1$ of the cannula 13 (shown in FIG. 3) so that the surgical instrument 36 is both axially slideable and rotationally positionable within the lumen 20 in cannula 13.

Typically, the dimensional differences may be on the order of a few thousands of an inch. As can be seen by the FIG. 6 the coaction between the exterior surface 36a of instrument shaft 36 and the interior web faces 14a-f creates a set of triangular shaped peripheral insufflation gas passages 30a-f that are located at the junction of adjacent web faces. In addition, the web faces 14a-f form a centering guide for maintaining the instrument 36 in axial alignment with a central axis of the cannula 13 to minimize trocar seal breakdown and consequent pressure loss between the surgical instrument and the cannula since less stress is placed on a trocar seal, which surrounds the medical instrument to seal and prevent insufflation gas from escaping through the trocar. As can be seen in FIG. 6 the difference in the cross sectional shape between the cylindrical instrument shaft 36 and the hexagonal cannula 13 creates a set of triangular shaped peripheral fluid passages 30a-f therebetween that allows the presence of both fluid flow and a medical instrument within the lumen of the cannula 13. In this example the internal web faces 14a-f of cannula 13 provide guides for maintaining the shaft 36 in a central location in lumen 20. That is, the web faces 14a-f limit shaft 36 from becoming misaligned or askewed within the lumen 20 of cannula 13, a feature which inhibits the accidental disturbance of a trocar seal between the shaft 36 of the medical instrument and the trocar housing 10 since less stress is placed on the seal, however, it also ensures that, each of the set of peripheral flow passages 30a-f remain open for fluid flow therethrough since the dissimilar shape of the cylindrical shaft 36 and the hexagonal cannula 13 prevent any of the peripheral passages from being blocked by shaft 36 if the shaft is located in an askew position within the lumen in cannula 13 since the shaft 36 is centrally constrained by web faces 14a-f.

A reference to FIG. 7, which is taken along lines 7-7 of FIG. 5 reveals the relationship between cylindrical medical instrument 36 and a second hexagonal shaped cannula 48. The cannula 48 is similar to the hexagonal cannula 13 of FIG. 1 except the corners of cannula 48 are radiused and the cannula webs 45a-f are not flat but concave inward. FIG. 7 also reveals a plastic flow of body tissue 39a around the exterior hexagonal surface of the cannula 48. That is, the varying radial dimensions of polygonal cannula 48 allow the body tissue 39a to flow away from points of high stress at the corners 46a-f of the polygonal shaped cannula 48 to areas of lower stress adjacent the webs 45a-f of the cannula 48, a feature not found in a cannula having a circular cross sectional shape since the tissue surrounding the circular cannula remains in the same high stressed condition all 360 degrees around the periphery of a circular cannula.

FIG. 7 shows the dimension from the geometric center of the shaft 36 to the outer cylindrical surface is designated by $R_6$ with $R_6$ having a dimension less than the polygonal cannula dimension $R_1$ to enable the medical instrument shaft 36 to be slideable disposed within the polygonal cannula 48 and at the same time provide a set of peripheral fluid passages 47a-f located in a spaced condition around the periphery surface 36a of the shaft 36 with the largest dimensions of the passages located at the junction of adjacent webs.

If both the cannula and the medical instrument contain a similar cross sectional shape, i.e. such as a circular configuration, the medical instrument and the cannula coact to form an annular fluid passage between the interior surface of the cannula and the exterior surface of the medical instrument. In such a trocar assembly the medical instrument can become skewed with respect to a central axis of the cannula which also distorts the annular flow passage introducing lateral fluid flow as well as axial fluid flow around the medical instrument, which can result in increased pressure losses due to an extended flow path past the medical instrument. However, by maintaining the peripheral passages in an open condition through the use of a dissimilar shape of a medical instrument and a cannula one prevents shutting off axial flow along a portion of the medical instrument thus limiting pressure losses due to the lateral flow between the cannula and the medical instrument. Consequently, if pressure losses due to lateral flow are eliminated one can use a cannula with a smaller cross sectional area than if the cannula and the medical instrument had a similar shape. Thus a feature of a cannula and a medical instrument having dissimilar shapes is that one minimizes pressure losses due to minimizing or eliminating lateral or circumferential flow around the medical instrument since the peripheral longitudinal flow passages remain in an open condition regardless of the position of the medical instrument in the cannula.

The use of a polygonal shape cannula allows one to minimize trauma to a patient in relation to a conventional "oversized" circular cannula. As used herein the term "oversized" cannula refers to a cannula having a circular cross section, which is used with a medical instrument having a circular cross section to form an annular insufflation gas passage along the medical instrument. To minimize pressure losses in the cannula and maintain a body cavity in an inflated condition the cross sectional area of the annular passage must be sufficiently large so that the pressure losses or the velocity of the insufflating gas flowing past the medical instrument remain relatively constant as the annular passage becomes distorted or partially blocked off as the medical instrument is periodically skewed with respect to a central axis of the lumen. Since skewing of the medical instrument occurs during the medical procedure the medical instrument skewing can increase the flow resistance and the velocity of the insufflation gas in the cross sectional area. To avoid pressure losses the annular passage is normally maintained larger i.e. "oversized" than if the medical instrument were to remain in a central location within the cannula.

A benefit of the polygonal shape cannula is that it can eliminate or inhibit pressure losses due to skewing of a medical instrument, which allows one to have a polygonal shaped cannula with a smaller cross sectional area than a circular cannula. A further feature of the polygonal cannula is that it also minimizes trauma to the patient since the polygonal cannula does not spread the insertion site tissue as greatly as a cylindrical oversized cannula even though each cannula may have the same maximum radial dimension. That is, a polygonal shaped cannula is able to allow the tissue to expand or flow laterally between the lobes or radiused corners which are located on the outside of the cannula thus limiting the tissue trauma around the cannula.

Thus, the use of a cannula having a different cross sectional shape than the medical instrument minimizes the pressure losses in comparison to the pressure losses occurring in a trocar where the cannula and the medical instrument have the same cross sectional shape.

Typically, most laparoscopic medical instruments have a round cross section, and are sized such that they fit into a targeted oversized circular cannula. By designing the cannula to have a shape that contains elongated peripheral flow passages that can maintain axial peripheral fluid around the exterior of the medical instrument even though the medical instrument may become skewed with respect to the axis of the cannula minimizes the pressure losses that occur with an oversized cannula. Thus a feature of the invention is that it eliminates the need for an oversized circular cannula and hence the disadvantages of an oversized circular cannula.

An advantage of a non-circular lumen cross section versus an "oversized" circular cross section is that the faces of the polygonal cannula coact to constrain or center a circular medical instrument within a lumen in the cannula, thus allowing the internal peripheral fluid passages in the cannula to continually remain open to gas flow therethrough.

An additional benefit for concentrically restraining a large medical instrument, within a noncircular cannula as opposed to having both a circular cross section of the instrument and a circular cross section of an oversized lumen, is the positive effect on the trocar seal located between the medical instrument and the trocar since the seal remains concentrically positioned around the cannula. Often times an instrument with a circular cross section, which is contained within an oversized cannula having a circular lumen can become canted or skewed with respect to a central axis of the cannula and the cannula seal which can stress the seal therebetween which may cause seal failure or reduced seal performance.

In the examples shown the cannula has a hexagonal shape with radiused corners and webs located between the radiused corners. In one case the webs are flat panels and in another case the webs have a concave shape. While a hexagonal shaped cannula is a preferred polygonal shape cannula other polygonal shaped cannulas of three or more sides may be used where the cross sectional shape is different from the cross sectional shape of the medical instrument without departing from the spirit and scope of the invention. In addition, medical instruments having an elliptical cross sectional shape may also be used to concentrically support the medical instrument therein while providing multiple longitudinal fluid passages along peripheral regions of the cannula. While laparoscopic procedures can be performed the trocar and cannula can be adapted for other forms of endoscopic surgery and is not limited to laparoscopic surgery.

We claim:

1. A trocar assembly comprising:
an instrument for performance of a medical function within a body cavity wherein a portion of the instrument is located external to the body cavity and a further portion is located internal to the body cavity; and
a cannula having a cyclic polygonal tube with a cyclic polygonal external shape for receiving the instrument, said a cyclic polygonal tube having a set of elongated concave panels each having a body tissue engaging inwardly concaving exterior surface and an edge with each of the edges integrally joined to an adjacent web at a radiused corner to form a polygonal lumen within the cannula with the cannula having at least three corners, said cannula comprises a different geometrical cross sectional shape then the cross sectional shape of the instrument with the instrument rotationally positionable within the cannula to provide a set of circumferential spaced peripheral gas passages between an inner surface of the cannula and an exterior surface of the instrument.

2. The trocar assembly of claim 1 wherein the instrument has an exterior surface for centrally locating the instrument within the lumen of the polygonal tube.

3. The trocar assembly of claim 1 wherein the polygonal tube has external radiused corners.

4. The trocar assembly of claim 1 wherein the instrument has a circular cross section.

5. The trocar assembly of claim 1 wherein the instrument is slidably and rotationally disposed within the polygonal tube.

6. The trocar assembly of claim 1 wherein the instrument is slidably disposed for insertion of the instrument into the lumen within the cannula.

7. A trocar assembly comprising:
an instrument for performance of a medical function within a body cavity wherein a portion of the instrument is located external to the body cavity and a further portion is located internal to the body cavity; and
a cannula having a cyclic polygonal tube with a cyclic polygonal external shape for receiving the instrument, said a cyclic polygonal tube having a set of elongated concave panels each having a body tissue engaging inwardly concaving exterior surface and an edge with each of the edges integrally joined to an adjacent web at a radiused corner to form a polygonal lumen within the cannula, said cannula comprises a different geometrical cross sectional shape then the cross sectional shape of the instrument with the instrument wherein the instrument comprises an obturator that is slidably removable from the cannula.

* * * * *